(12) United States Patent
Massaro

(10) Patent No.: US 8,480,953 B2
(45) Date of Patent: Jul. 9, 2013

(54) SYSTEM AND METHOD FOR VESSEL ALIGNMENT

(75) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 415 days.

(21) Appl. No.: 12/469,219

(22) Filed: May 20, 2009

(65) Prior Publication Data

US 2010/0294050 A1    Nov. 25, 2010

(51) Int. Cl.
*C12Q 1/68* (2006.01)

(52) U.S. Cl.
USPC .......... 422/50; 422/941; 422/942; 422/913; 73/864.91; 73/863

(58) Field of Classification Search
USPC ............ 422/941, 942, 913, 500, 501, 502, 422/503, 504; 235/462.1–462.49; 356/246
See application file for complete search history.

(56) References Cited

U.S. PATENT DOCUMENTS

| | | |
|---|---|---|
| 4,056,361 A | 11/1977 | Peters et al. |
| 4,371,498 A | 2/1983 | Scardato et al. |
| 5,098,661 A | 3/1992 | Froehlich et al. |
| 5,224,585 A | 7/1993 | Blanco et al. |
| 5,357,095 A | 10/1994 | Weyrauch et al. |
| 5,456,887 A | 10/1995 | Calvo et al. |
| 5,663,545 A | 9/1997 | Marquiss et al. |
| 5,919,553 A | 7/1999 | Kavanaugh |
| 6,161,759 A * | 12/2000 | Moss et al. ............... 235/462.01 |
| 6,293,750 B1 * | 9/2001 | Cohen et al. .............. 414/744.4 |
| 6,598,796 B2 * | 7/2003 | Harrop ..................... 235/462.01 |
| 6,890,759 B2 | 5/2005 | Bierre et al. |
| 2002/0102362 A1 | 8/2002 | Schneider |
| 2006/0000296 A1 | 1/2006 | Salter |
| 2006/0263248 A1 | 11/2006 | Gomm et al. |
| 2008/0318323 A1 * | 12/2008 | Shintani et al. ................. 422/63 |

FOREIGN PATENT DOCUMENTS

| | | |
|---|---|---|
| EP | 1142643 A | 10/2001 |
| EP | 1224977 A1 | 7/2002 |
| FR | 2764704 A1 | 12/1998 |
| GB | 1512845 | 6/1978 |
| JP | 57-16359 | 1/1982 |

OTHER PUBLICATIONS

International Search Report and Written Opinion from PCT Application No. PCT/US2010/001440 dated Aug. 20, 2010.

* cited by examiner

*Primary Examiner* — In Suk Bullock
*Assistant Examiner* — Sharon Pregler
(74) *Attorney, Agent, or Firm* — Wolf, Greenfield & Sacks, P.C.

(57) ABSTRACT

A vessel including an identification region may be placed in a holder. Through interaction of a positioning feature on the vessel and an orientation feature on the holder, the vessel can be placed into an alignment orientation, e.g., such that the identification region may be reliably read by a reader. The identification region may provides information related to the sample, such as vessel identity, sample volume, processes to be performed on the sample, and so on.

15 Claims, 14 Drawing Sheets

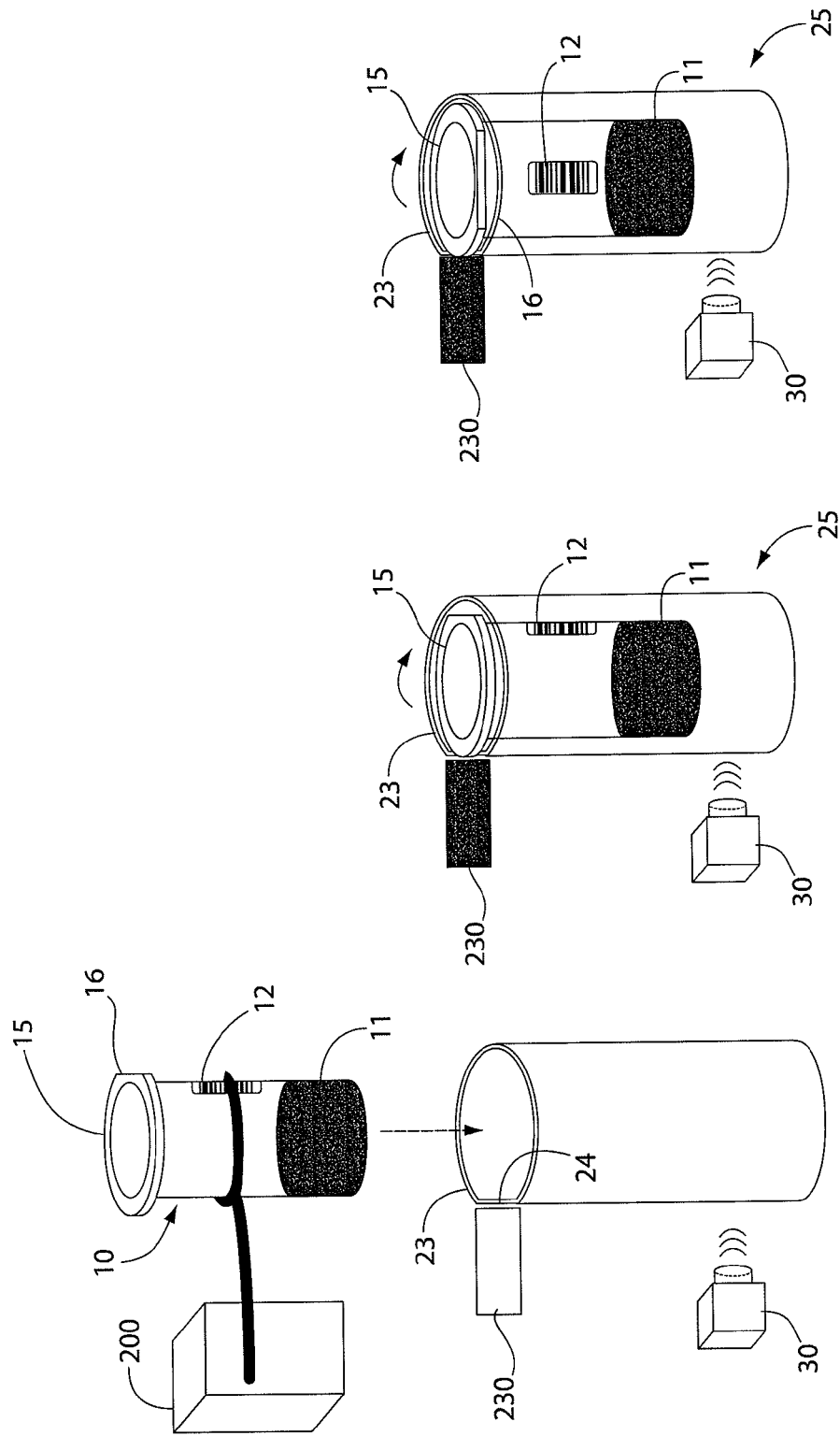

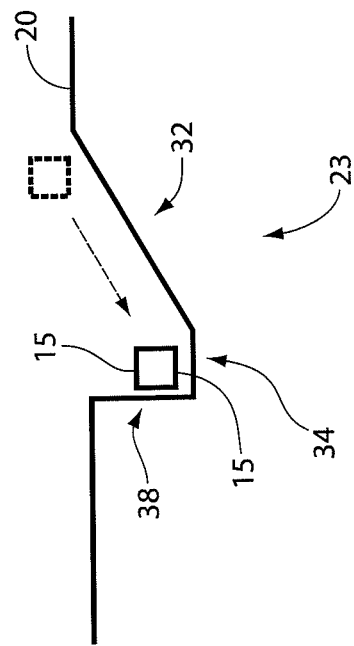
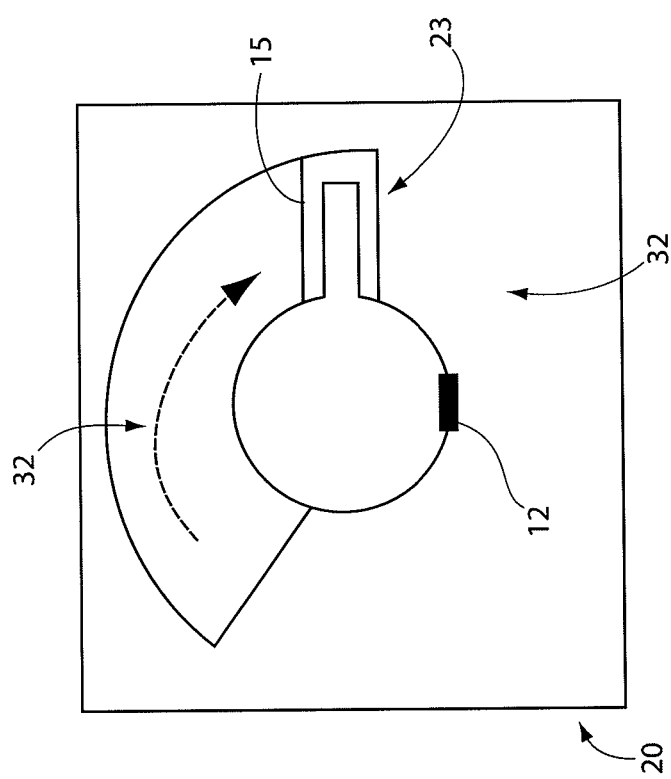
Fig. 19
Fig. 18 ically placed within vessels that are themselves held by a rack, robotic manipulator or other holder so that the vessels can be subsequently processed downstream. Vessels are often marked, for example with a barcode, so that an optical scanner can identify each vessel by its marking, e.g., before the vessel is placed into a rack.

SYSTEM AND METHOD FOR VESSEL ALIGNMENT

BACKGROUND OF INVENTION

1. Field of the Invention

Systems and methods for automatic alignment of a vessel with respect to a holder are generally disclosed.

2. Related Art

Samples that are used for research and analysis applications are commonly placed within vessels that are themselves held by a rack, robotic manipulator or other holder so that the vessels can be subsequently processed downstream. Vessels are often marked, for example with a barcode, so that an optical scanner can identify each vessel by its marking, e.g., before the vessel is placed into a rack.

SUMMARY OF INVENTION

The inventor has appreciated that for some applications, reliable identification of vessels and/or samples within vessels that are placed in a rack or other holder can be important to do in a high throughput manner. In some aspects presented herein, a vessel having a sample (such as a blood sample) and an identification region (such as a bar code) is placed in a holder. The holder may be a relatively stationary element, such as a tube rack, multiwall plate, carousel, etc., or may be a more mobile element, such as a robotic manipulator, conveyor or other transport. The identification region, when read, may provide information related to the sample within the vessel, e.g., an identity of the vessel, an origin of the sample, and so on. By virtue of a positioning feature on the vessel and an orienting feature on the holder, the vessel may be automatically placed into an alignment orientation. When the vessel is in or moved to the alignment orientation, the identification region of the vessel may be exposed or otherwise located relative to a reader so the identification region can be read reliably. In other embodiments, positioning of the vessel at the alignment orientation may facilitate further physical handling of the vessel, e.g., a vessel in a known alignment orientation may be transferred from the holder to another device, such as a vessel transport. Since the vessel may be transferred in a known orientation, further reading of the identification region or other handling of the vessel may be accomplished in a desired way.

In one illustrative embodiment, a system for handling and analyzing samples is provided. The system may include a vessel for holding at least one biological sample, such as a blood sample taken from a body. The vessel may include an identification region for providing information related to the at least one sample and a positioning feature for use in orienting the vessel in an alignment orientation. A holder may be arranged to receive the vessel at a location and include an orienting feature that complements or otherwise interacts with the positioning feature of the vessel such that when the holder receives the vessel, the vessel is placed in the alignment orientation relative to the holder. A reader may read the identification region of the vessel and store information related to the at least one sample when the vessel is in, or moved to, the alignment orientation.

In another illustrative embodiment, a method for handling and analyzing samples is provided. The method includes providing a vessel for holding at least one sample where the vessel includes an identification region that provides information related to the at least one sample. The vessel may be placed in a holder and the vessel may be aligned with respect to the holder using a positioning feature of the vessel and an orienting feature of the holder that interacts with the positioning feature. Thus, when the holder receives the vessel, the vessel may be placed in an alignment orientation relative to the holder. The identification region of the vessel may be read, and information related to the at least one sample may be stored.

Other advantages and novel features of the present invention will become apparent from the following detailed description of various non-limiting embodiments of the invention when considered in conjunction with the accompanying figures and from the claims.

BRIEF DESCRIPTION OF THE DRAWINGS

Aspects of the invention are described with reference to the following drawings in which numerals reference-like elements, and wherein:

FIG. 4 is a side view of a vessel held by a vessel manipulator prior to being placed in a holder in accordance with aspects of the invention;

FIG. 5 is a side view of the vessel of FIG. 4 placed in the holder and being rotated in accordance with aspects of the invention;

FIG. 6 is a side view of the vessel of FIG. 4 placed in the holder and being rotated further in accordance with aspects of the invention;

FIG. 18 is a top view of a vessel having a positioning feature and being in an aligned orientation in a holder and the positioning feature being adjacent to a stop feature in accordance with aspects of the invention;

FIG. 19 is a schematic side view of the vessel of FIG. 18 having the positioning feature and being in an aligned orientation in the holder;

DETAILED DESCRIPTION

Figure 1:
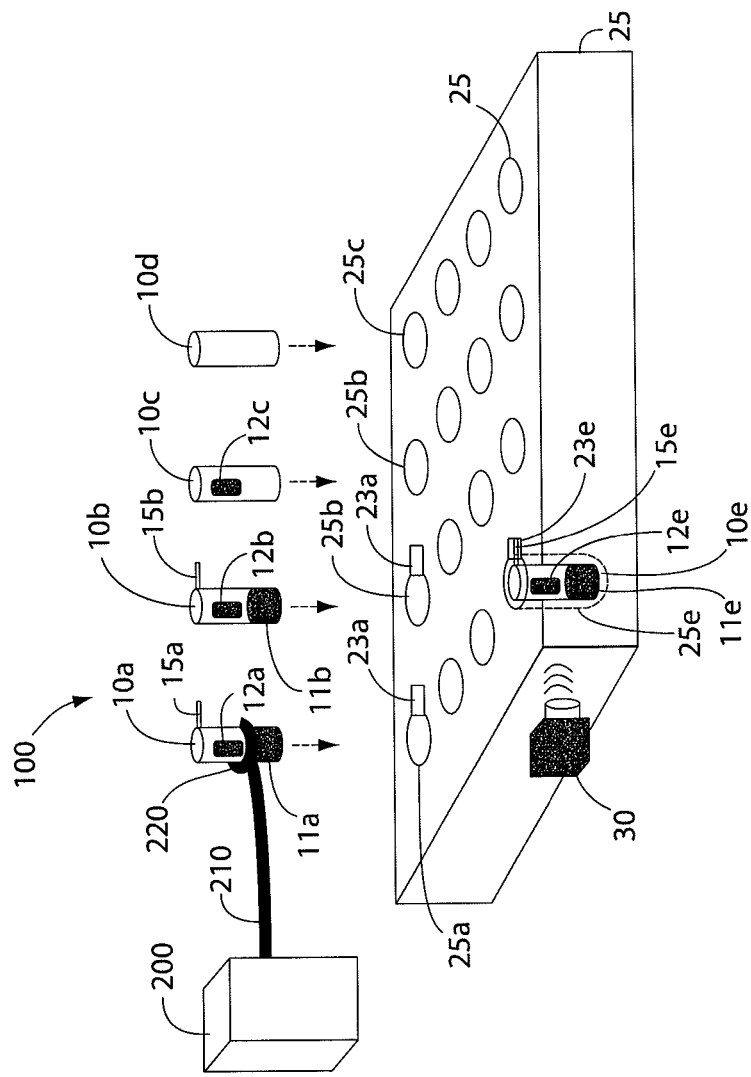
FIG. 1 is a schematic view of an embodiment of a system for handling and analyzing samples in accordance with aspects of the invention.

Aspects of the invention described herein are directed generally to orientation and/or identification of vessels placed in a holder, e.g., for biological and medically-related applications. Various illustrative embodiments are described below with reference to particular applications. However, it should be understood that the following description is not limited in its application to the details of construction and the arrangement of components set forth in the following description or illustrated in the drawings. Other embodiments may be employed and aspects of the inventions may be practiced or carried out in various ways. For example, vessels may be used to carry any suitable material, such as drugs used in screening applications, minerals used to assess the composition of rocks or similar substances, and so on, and are not limited to carrying blood or other body or tissue samples.

In some illustrative embodiments, a vessel having a sample can be reliably identified through features that provide for automatic alignment of an identification region of the vessel with a reader. In some embodiments, the vessel may include a positioning feature such that upon placement of the vessel in a holder, the vessel may be automatically placed into an alignment orientation such that the identification region can be suitably read by the reader. In one embodiment, the holder may include an orienting feature that complements the positioning feature of the vessel and aids in locating the vessel in the alignment orientation. Through automatic alignment of the vessel, studies that employ a large number of sample vessels may at least have vessel identification performed reliably in a high throughput, efficient manner.

By way of example, FIG. 1 shows a system 100 for handling sample vessels 10. In this embodiment, each of the vessels 10 includes a positioning feature 15 that may be used to help orient a vessel 10 when placed in a holder 20, such as a rack-like arrangement shown in FIG. 1. Vessels 10 may or may not include samples 11, such as a blood sample, and/or an identification region 12, such as a bar code. For example, vessels 10a, 10b and 10e are shown to include samples 11a, 11b, and 11e, respectively, whereas samples 11 are not provided in vessels 10c and 10d. In addition, vessels 10a, 10b, 10c, and 10e are shown to include identification regions 12, while vessel 10d does not have an identification region 12. In this illustrative embodiment, the holder 20 includes a plurality of locations 25 where a vessel 10 may be received, and each location 25 has a corresponding orientation feature 23. The locations 25 are formed as a generally cylindrically-shaped opening to receive the tubular vessels 10, and the orientation feature 23 at each location 25 has a slot-like opening to receive a tab-shaped positioning feature 15 of a corresponding vessel 10. However, as described in more detail below, the shape, size and/or other characteristics of the vessels 10, holder 20, positioning features 15 and orientation features 23 may have any other suitable arrangement.

In accordance with an aspect of the invention, when a vessel 10 having a positioning feature 15 is placed in a holder 20 having a orientation feature 23, the positioning feature 15 of the vessel 10 and the orientation feature 23 of the holder 20 may interact so that the vessel 10 is placed in a suitable alignment orientation relative to the holder 20. In this example, the tab-like positioning feature 15 of the vessel 10 may be received in the slot-like opening of the orientation feature 23 so that the vessel 10 is oriented (in a rotary sense about the vessel's longitudinal axis) in a desired way relative to the holder 20. Positioning of the vessel 10 in an alignment orientation, i.e., a known orientation relative to the holder 20, may provide benefits, such as properly positioning an identification feature 12 for reading, and/or positioning the vessel 10 in a known way so that other components can properly interact with the vessel. For example, in some circumstances, a vessel in a known orientation may be more reliably picked up and removed from the holder 20 by a robotic manipulator. In some cases described in more detail below, interaction between a positioning feature 15 and an orientation feature 23 may allow for the vessel 10 to be automatically placed in an appropriate alignment orientation, e.g., the positioning and orientation features may interact to cause movement of the vessel 10 to the alignment orientation.

The vessels 10 may be manipulated by hand when placed in the holder 20, e.g., an operator may place individual vessels 10 into locations 25 of a holder 20 like that in FIG. 1, or the vessels 10 may be placed by an automated system. For example, FIG. 1 shows a vessel manipulator 200 that has the general form of a robotic device with an arm 210 and gripper 220 that may be used to physically manipulate one or more vessels 10. The vessel manipulator 200 may be arranged to move vessels 10 with any suitable degree(s) of freedom, such as moving vessels 10 linearly, rotating vessels 10 about any suitable axis or axes, and so on. For example, a vessel manipulator 200 may grasp vessel 10a, position the vessel 10a over a suitable location 25a, and place the vessel 10 in the holder 20. When placing the vessel 10, the vessel manipulator 200 may lower the vessel 10a into the location 25a, or may drop the vessel 10a from a point above the location 25a. As used herein, a vessel is received by a holder when the vessel is at least partially associated with the holder so that the holder may have at least some influence on the position of the vessel. In this respect, the holder may be considered to have received the vessel without the vessel being fully engaged by, and oriented with respect to, the holder. Similarly, when a vessel is said to be "in" a holder, it is understood to refer to conditions including where the vessel is received by the holder as well as when the vessel is at an alignment orientation. As described in more detail below, the vessel 10 may be placed into a location 25 at or near a desired orientation (e.g., so that the positioning feature 15a and orientation feature 23a of the vessel 10a are engaged), or the vessel 10 may be placed into a location 25 without any, or a more limited, regard to its orientation (e.g., such that the positioning feature 15a and orientation feature 23a of the vessel 10a are not engaged). For example, the manipulator 200 may place vessels 10 so that a lower end is generally received at the location 25, but the rotational position of the vessel 10 about its longitudinal axis may not be controlled, e.g., so that the positioning feature 15 and the orientation feature 23 are not aligned. Such placement techniques may be used, for example, when the positioning and orientation features are arranged to interact so as to cause movement of the vessel to an alignment orientation. In other embodiments, the manipulator 200 or user may place the vessel at a location 25 so that the positioning feature 15 and the orientation feature 23 are engaged and the vessel 10 is in the alignment orientation.

As mentioned above, interaction of the positioning feature 15 and counterpart orientation feature 23 at a location 25 of a holder 20 may orient the vessel 10 so that the identification region 12, if present, may be read by a reader 30. The identification region 12 and reader 30 may take any suitable form so that the identification region 12 may exchange information to the reader 30 in one-way or two-way fashion. For example, the identification region 12 may include a barcode or other marking that is read by the reader 30, e.g., using a scanning laser, video camera or other imaging device and associated image analysis circuitry, or other arrangement. Markings used for identification regions 12 may be made by any suitable method, such as written by hand or formed by a machine that etches, prints, applies a label or otherwise forms the marking. In other embodiments, the identification region 12 may include an active or passive RFID tag or other device that is capable of communicating with the reader 30 using electromagnetic radiation or other suitable medium. In another embodiment, the identification region 12 may include physical structures that may be contacted by the reader 30, e.g., an arrangement of bumps, grooves, tabs or other features, that may be interpreted by the reader 30 in a way similar to how a lock can detect the physical features of a key. Alternately, the reader 30 may electrically contact the identification region 12, e.g., to detect a resistance or other electrical characteristic that represents information. Other identification region 12 arrangements are possible, including those using infrared light communication, wireless electronic communication, and so on.

Information related to the sample 11 that is represented by the identification region 12 may relate to any desired characteristic of the vessel and/or the sample. In some embodiments, the information may relate to particular chemical, biological and/or other properties of the sample, e.g., an identity of the person from which the sample was taken, a blood type, a volume of the sample, chemical identity, cell characteristics, molecular properties, and/or the like. Such information may or may not be unique to each sample. In some embodiments, the information may relate to identification of the particular vessel, e.g., representing a vessel identity, vessel size, shape or other characteristics, and so on. In some cases, the identification region 12 may include information based on the type of test or analysis performed or to be performed on the sample. For example, prior to testing of a sample, the identification region may relate to the specific vessel that is being used. After a sample is tested and placed in the vessel, the identification region may be updated, by any suitable method, so that information related to the nature of the vessel and/or the sample within the vessel may be appropriately identified.

In some embodiments, an identification region may be suitably provided on the vessel after the sample is placed in the vessel. The identification region 12 may include the actual information itself, e.g., a name of a person, the actual sample volume, etc., or the identification region 12 may include a reference used to locate or otherwise determine such information, e.g., the identification region 12 may include a number or other alphanumeric string that can be used as an address to locate corresponding information in an appropriate database or other store. Information read from an identification region 12 may be stored or otherwise used, as desired. As an example, the information conveyed by an identification region of a vessel to a reader may be stored as electronic data by an computer storage device associated with the reader 30, e.g., an alphanumeric string read from the identification region 12 may be stored together with other information regarding the vessel, such as its location in a holder, and so on.

The reader 30 may be arranged to read the identification region 12 of one or more vessels 10 in a holder 20, if the holder 20 includes more than one location 25. In some embodiments, the holder 20 may be translucent or transparent to electromagnetic radiation used by the reader 30 to read identification regions 12. In other embodiments, the holder 20 may have a window or other opening to permit the passage of radiation or other components for reading an identification region 12, as necessary. In other embodiments, the reader 30 may have components mounted to the holder 20, e.g., for reading identification regions 12 on vessels 10 located away from the outer periphery of the holder 20. For example, the reader 30 may include an imaging device, set of electrical contacts or other sensor for each location 25 so that the identification region 12 for each vessel 10 may be read by a single corresponding sensor. In certain cases, the reader 30 may be able to read an identification region 12 even if the identification region 12 is not directly facing the reader 30 or otherwise positioned ideally for reading purposes. For example, the identification region 12 may not necessarily be ideally positioned for reading, but the reader 30 may be capable of reading the identification region 12 anyway, e.g., in the case of an RFID tag/reader arrangement. However, in general, desired engagement between the positioning feature 15 and the orientation feature 23 may position the vessel 10 so that the reader 30 can more reliably read the identification region 12.

Figure 2:
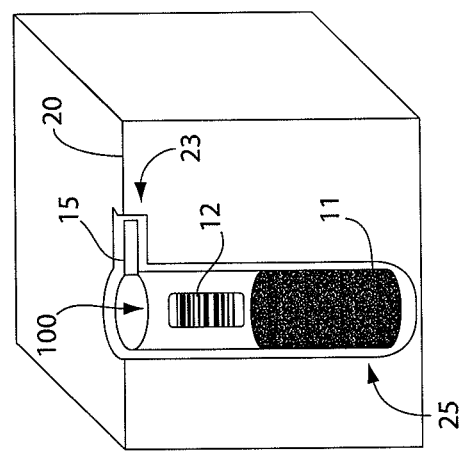
FIG. 2 is a perspective view of a vessel having a positioning feature and being disposed in a holder in accordance with aspects of the invention.

Engagement of a positioning feature with an orientation feature may help orient or fix the position of the vessel in one or more directions (e.g., one or more linear directions, rotational directions or others). FIG. 2 shows a cross-sectional view of a location 25 of the holder 20 in FIG. 1, along with further detail regarding the tab-like positioning feature 15 engaged with a respective orientation feature 23, which has a slot-like shape. When the positioning feature 15 of the vessel 10 in this embodiment is received by the orientation feature 23, the vessel 10 may be oriented both rotationally (so that the identification feature 12 is suitably located for interaction with a reader 30) and axially (in an up and down direction along the longitudinal axis of the vessel 10) so the vessel 10 is located at a desired depth at the location 25. Alternately, the vessel 10 may be supported at its bottom end by the holder 20 instead of being supported axially by the positioning feature 15.

Although in the embodiment shown the positioning feature 15 includes a tab-like extension that extends radially from the vessel 10, it should be appreciated that the positioning feature 15 may be any appropriate size, shape or design, and may help orient the vessel in one or more directions relative to the holder 20. For example, the positioning feature 15 may have a triangular shape, have multiple element projections, be curved, have sharp edges, or combinations thereof. Likewise, the orientation feature 23 may have a size, shape or other features that complement the positioning feature 15, and may complement the shape of a plurality of different types of positioning features 15. For example, the vessel 10 may have a plurality of tab extensions and be placed in the holder 20 such that the extensions of the positioning feature 15 reside in slots of the orientation feature 23. The tab-like extensions may extend away from one another in opposite directions, could extend perpendicularly relative to each other, or at another angle. It should also be appreciated that structural features of a positioning feature 15 may be arranged opposite to that shown, e.g., so that the orientation feature 23 includes a tab or other extension that engages with a slot of the positioning feature 15 in the vessel 10.

Figure 3:
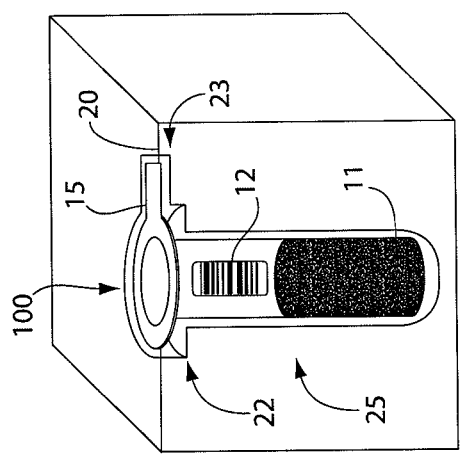
FIG. 3 is a perspective view of another vessel having a positioning feature and being disposed in a holder in accordance with aspects of the invention.

As another illustrative example, FIG. 3 shows an embodiment where the positioning feature 15 includes both a tab-like projection and a rim at the top of the vessel 10. The orientation feature 23 of the holder 20 may include a recess 22 to receive the rim of the positioning feature 15 in addition to the tab-like element. Engagement between the rim at the top of the vessel 10 and the recess 22 of the orientation feature 23 may help center the vessel 10 in the cylindrical hole at the location 25 and/or locate the vessel appropriately along its longitudinal axis relative to the holder 20, e.g., the rim may support the weight of the vessel 10. While not explicitly shown in FIGS. 1-3, the orientation feature and/or the positioning feature may include a beveled shape or other arrangement that helps the positioning feature more easily engage with the orientation feature. For example, the recess 22 in FIG. 3 may have a tapered or funnel-shaped upper region to aid in the proper reception of the positioning feature 15. In some embodiments, the holder and/or the vessel may be shaken, vibrated or otherwise moved to help aid interaction of the positioning feature and the orientation feature.

Figure 8:
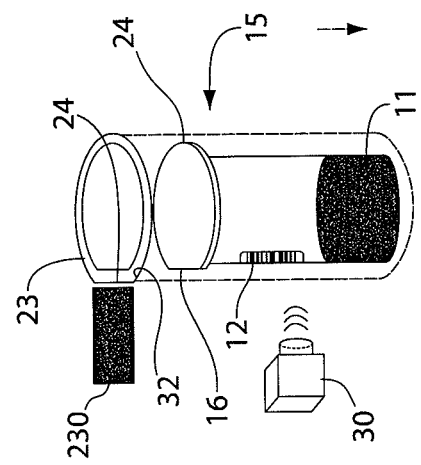
FIG. 8 is a side view of the vessel of FIG. 4 placed in the holder and the identification region being read in accordance with aspects of the invention.
Figure 11:
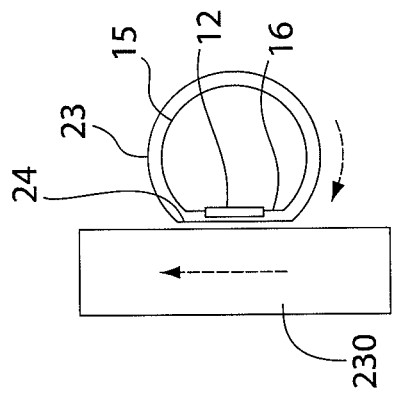
FIG. 11 is a top view of the embodiment of FIG. 7 with the vessel placed in the holder with the positioning feature and the orientation feature being aligned in accordance with aspects of the invention.
Figure 10:
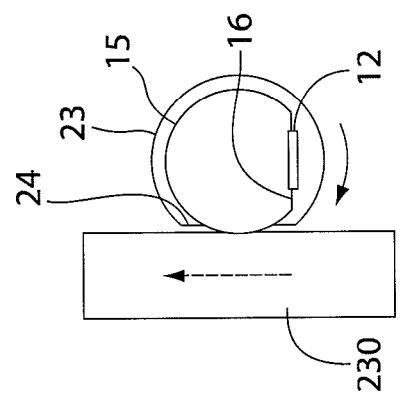
FIG. 10 is a top view of the embodiment of FIG. 6 with the vessel placed in the holder and being rotated further in accordance with aspects of the invention.
Figure 9:
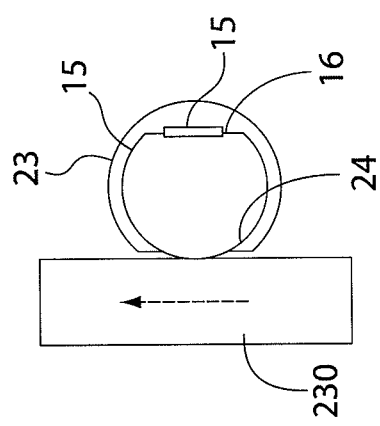
FIG. 9 is a top view of the embodiment of FIG. 5 with the vessel placed in the holder and being rotated in accordance with aspects of the invention.

Although some embodiments may require relatively careful placement of the vessel in a holder to engage the positioning and orientation features, in other embodiments, a vessel may be placed in a holder without regard for at least some aspects of the orientation of the vessel. FIGS. 4-11 show an illustrative embodiment in which a vessel 10 may be placed into a location 25 of a holder 20 without regard for at least a rotational aspect of the orientation of the vessel 10. In this embodiment, the vessel 10 has a positioning feature 15 that includes a circular rim at a top end of the vessel 10 with a flat portion 16. (FIGS. 9-11 show a top view of the vessel 10 and more clearly illustrate the "D" shape of the positioning feature 15.) The orientation feature 23 at the holder 20 includes a generally cylindrically-shaped opening with a flat section 24 that complements the positioning feature 15. In this embodiment, the vessel 10 is dropped into a location 25 of the holder 20 so that the flat 16 of the positioning feature 15 may or may not match up with the flat section 24 of the orientation feature 23 (see FIGS. 5 and 9). The size and shape of the positioning feature 15 and the orientation feature 23 are such that the vessel 10 does not fully drop into the opening at the location 25 until the positioning feature 15 aligns with the orientation feature 23 (i.e., the flats 16 and 24 align). Instead, the rim of the positioning feature 15 rides on the flat 24 of the orientation feature 23, preventing the vessel 10 from falling into the opening at the location 25, until the flats 16 and 24 are adjacent.

Figure 7:
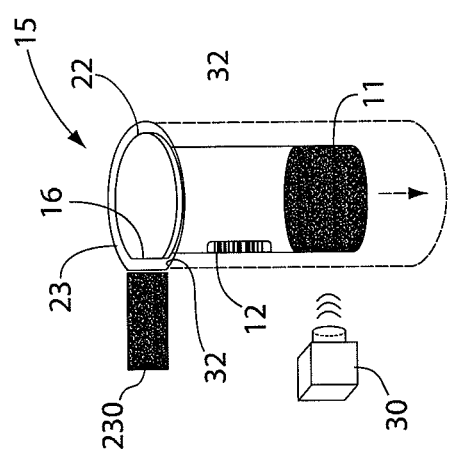
FIG. 7 is a side view of the vessel of FIG. 4 placed in the holder with the positioning feature and the orientation feature being aligned in accordance with aspects of the invention.

In this embodiment, the manipulator 200 includes a rotator 230 (such as a wheel or belt) that frictionally engages with the vessel 10 and rotates the vessel 10 (e.g., in a clockwise direction when looking down on the vessel 10 as in FIG. 9). Although the rotator 230 includes a motor-driven wheel or belt and engages the vessel 10 by friction at the rim, the rotator 230 may operate on the vessel 10 in other ways, such as by magnetic forces in attracting a magnet or magnetizable material on the vessel 10, by moving the orientation feature 23 (e.g., rotating the flat section 24) so as to engage the positioning feature 15, and so on. FIGS. 6 and 10 show the vessel 10 partially rotated, and FIGS. 7 and 11 show the vessel 10 fully rotated so that the positioning feature 15 aligns with the orientation feature 23. In this embodiment, once the positioning feature 15 and the orientation feature 23 are aligned, the vessel 10 drops further into the holder 20 as shown in FIG. 8, so that the bottom of the vessel 10 rests at the bottom of the opening of the holder 20. Of course, other arrangements are possible, such as those shown in FIGS. 2 and 3 where the vessel 10 is suspended at the location 25, for example. Upon suitable alignment of the positioning feature 15 and the orientation feature 23, the vessel 10 may drop into an alignment orientation such that a reader 30 is able to more reliably read the identification region 12 of the vessel 10.

It should be appreciated that an arrangement like that in FIGS. 4-11 may be used to orient and identify a vessel 10, and then transfer the vessel 10 to another portion of the manipulator 200 or other transport. For example, vessels 10 having random or unknown orientations and/or identities may be dropped into a location 25 like that in FIGS. 4-11 so that the vessel 10 can be properly oriented and have the identification region 12 is read. Thereafter, the now identified and oriented vessel 10 may be transferred to a robotic manipulator, carousel, or other device that further transports the vessel 10. For example, the vessel 10 in FIG. 8 may drop through the opening at the location 25 into another holder or manipulator located below the location 25. Since the orientation of the vessel is defined as it exits from the location, the downstream transport device may receive the vessel in a known orientation.

Figure 12:
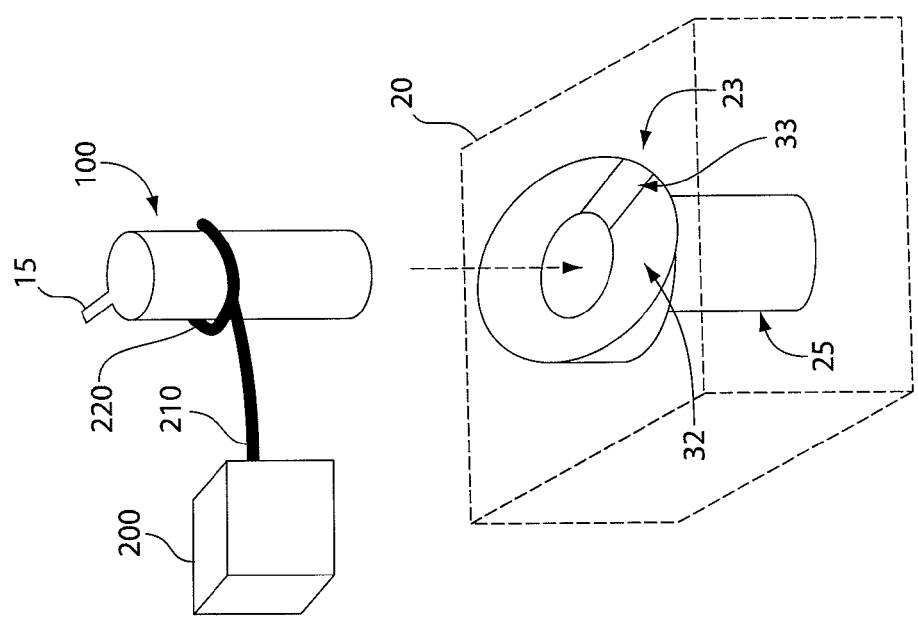
FIG. 12 is a perspective view of a vessel being held by a vessel manipulator and being located above a holder in accordance with aspects of the invention.
Figure 13:
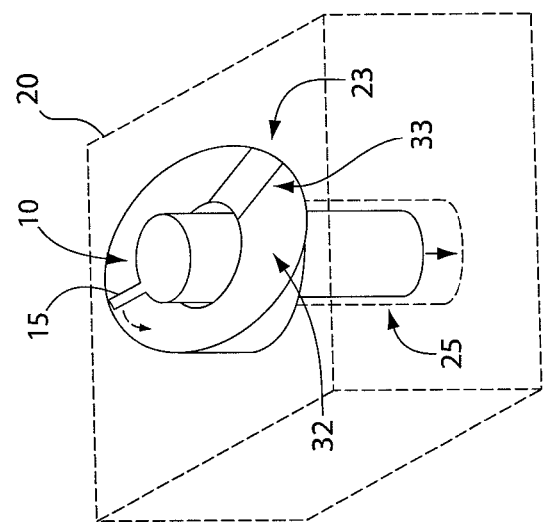
FIG. 13 is a perspective view of the vessel of FIG. 12 located in the holder and not being in an aligned orientation in accordance with aspects of the invention.
Figure 15:
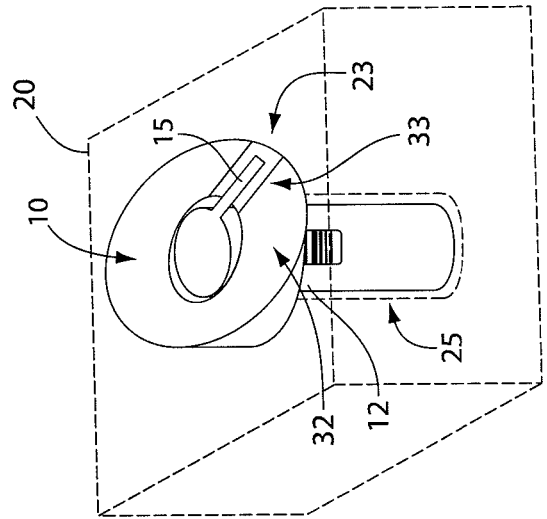
FIG. 15 is a perspective view of the vessel of FIG. 12 located in the holder and being in an aligned orientation in accordance with aspects of the invention.
Figure 14:
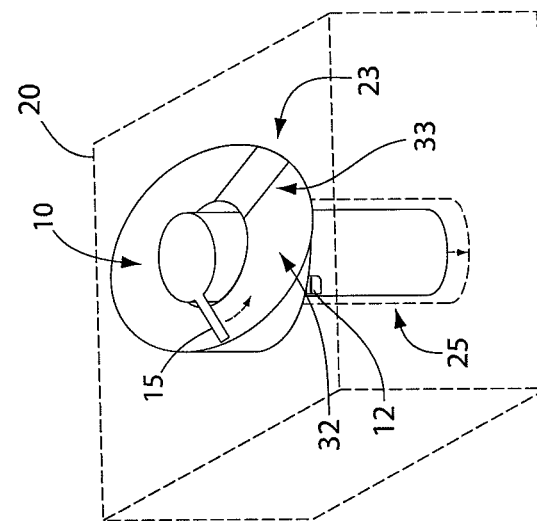
FIG. 14 is a perspective view of the vessel of FIG. 12 located in the holder and not being in an aligned orientation in accordance with aspects of the invention.

In some embodiments, the holder may include an orientation feature that is arranged to interact with the positioning feature of a vessel so as to move the vessel into an alignment orientation. Such an arrangement may eliminate the need for a manipulator, such as the rotator 230 in FIG. 4, to move the vessel 10 and/or the orientation feature 23 so as to cause the vessel to move to an alignment orientation. For example, FIGS. 12-15 show an illustrative orientation feature 23 that includes a slanted portion 32 that allows for the positioning feature 15 of the vessel 10 to effectively slide into a desired region of the orientation feature 23 of the holder 20 regardless of how the vessel is initially placed in the holder 20. As shown in FIG. 12, a vessel manipulator 200 may hold a vessel 10 with a positioning feature 15 above the holder 20 for placement at a particular location 25. In this embodiment, the positioning feature 15 has a tab-like shape extending from the vessel 10 like that in FIG. 1, but may be arranged in other suitable ways. The manipulator 200 (or a human operator) may drop or otherwise move the vessel 10 into the location 25 (e.g., in a direction along the dashed arrow) with or without regard for the relative position of the positioning feature 15 and the orientation feature 23. FIG. 13 shows the vessel 10 being received at the location 25 of the holder 20. In this example, the positioning feature 15 is located at a high side of the slanted portion 32. However, because of the arrangement of the positioning feature 15 and the orientation feature 23, the vessel 10 may tend to rotate (e.g., under the pull of gravity or other force) so that the positioning feature 15 is located at a low side of the slanted portion 32 (which in this case includes a slot-like groove 33). FIG. 14 shows the vessel 10 in the process of rotating (in a counterclockwise direction looking down on the vessel 10) so that the positioning feature 15 moves toward the slot 33. This rotation may be caused by gravity pulling down on the vessel 10 and/or another force, such as a rotator 230 like that in FIG. 4. FIG. 15 shows the positioning feature 15 of the vessel 10 received in the slot 33 and the vessel 10 in the alignment orientation. In this embodiment, the identification region 12 is now in view so as to be more reliably read by a reader 30. Alternately, the identification region 12 may be read as the vessel 10 moves toward the alignment orientation. As a result of this process, a vessel 10 that is originally not in a desired alignment orientation may be automatically brought into an alignment orientation in the holder 20.

Figure 17:
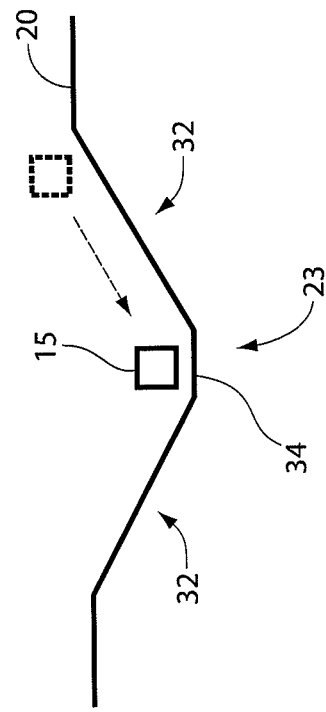
FIG. 17 is a schematic side view of the vessel of FIG. 16 having the positioning feature and being in an aligned orientation in the holder.
Figure 16:
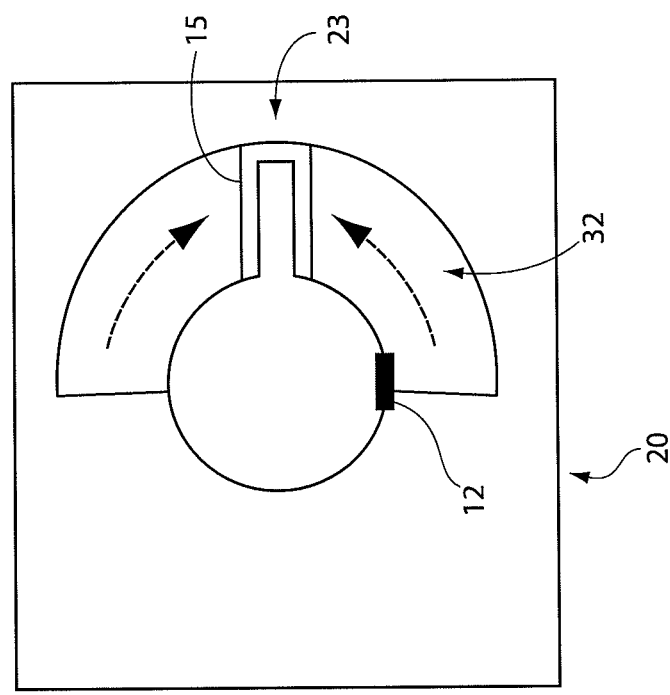
FIG. 16 is a top view of a vessel having a positioning feature and being in an aligned orientation in a holder and the positioning feature being adjacent to slanted portions of a orientation feature in accordance with aspects of the invention.

Although the orientation feature 23 of FIGS. 12-15 includes a slanted region 32 that is positioned entirely around the opening to receive the vessel 10, the slanted region 32 could be arranged in other ways. For example, FIGS. 16 and 17 show another illustrative embodiment where the orientation feature 23 extends only partially around the opening of the holder 20. A top view of the vessel 10 in the holder 20 illustrated by FIG. 16 shows that the orientation feature 23 includes slanted portions 32 on either side of a flat section 34 at a lowest point of the orientation feature 23. FIG. 17 shows a schematic cross-section illustration of a positioning feature 15 moving from an initial position (shown in dashed line) to a final position (shown in solid line) at the flat section 34 of the orientation feature 23. As shown, the orientation feature 23 extends approximately 180 degrees around the opening of the holder, i.e., about 90 degrees on either side of the lowest point of the orientation feature 23. However, it should be appreciated that the orientation feature may extend in any suitable arrangement direction around the opening of the holder as desired. For example, FIGS. 18 and 19 show an arrangement in which a slanted portion 32 extends about 120 degrees around the opening for the vessel 10 and is located on only one side of a flat section 34. The orientation feature 23 also includes a stop feature 38 that stops the positioning feature 15, as necessary, at the flat section 34 after moving down the slanted portion 32.

Figure 21:
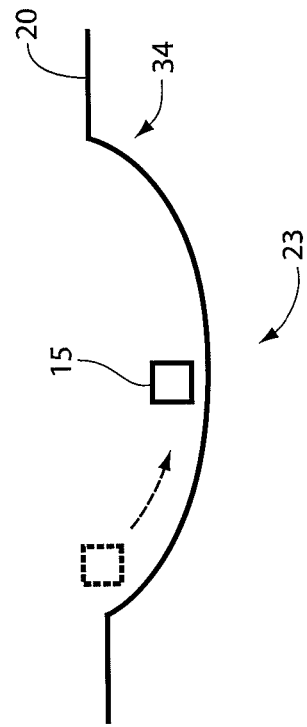
FIG. 21 is a schematic side view of the vessel of FIG. 20 having a positioning feature being associated with a orientation feature in accordance with aspects of the invention.
Figure 20:
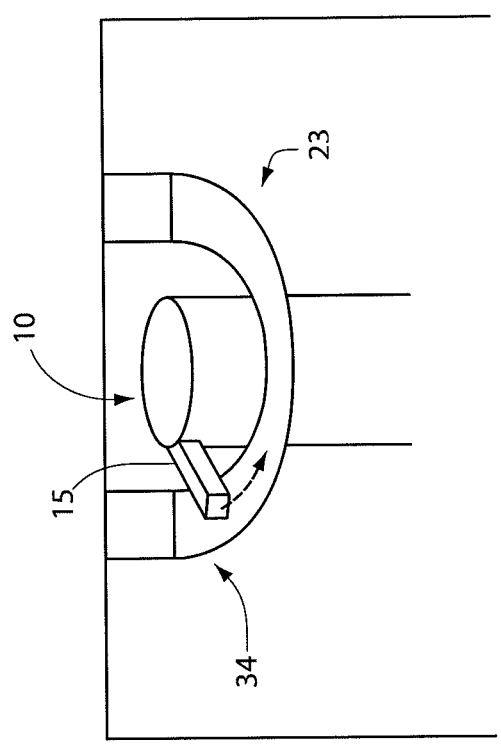
FIG. 20 is a perspective view of a vessel having a positioning feature being associated with a orientation feature in accordance with another aspect of the invention.

As one of skill in the art will appreciate, a reader 30 may be able to read an identification region 12 when the region 12 is in sufficiently close proximity and orientation with respect to the reader 30. As such, the identification region 12 need not be positioned at a precise location, and thus a positioning feature 15 may not be required to engage with a specific region of the orientation feature 23, such as a flat section 34 or slot 33 in FIGS. 12-19. Thus, as shown in FIGS. 20 and 21, the orientation feature 23 need not include a defined stop area for the positioning feature 15, but instead may include a sloped region 34 that has a continuously curved shape. As can be seen in FIGS. 20 and 21, the positioning feature 15 of a vessel may move from higher regions of the sloped region 34 to a generally lower area, e.g., under the pull of gravity along with vibratory movement of the holder 20. This movement may not necessarily locate the positioning feature 15 at the same position relative to the holder 20 every time, but may position the identification region 12 suitably close to an alignment orientation, e.g., to allow reading of the identification region 12 by the reader 30.

Figure 23:
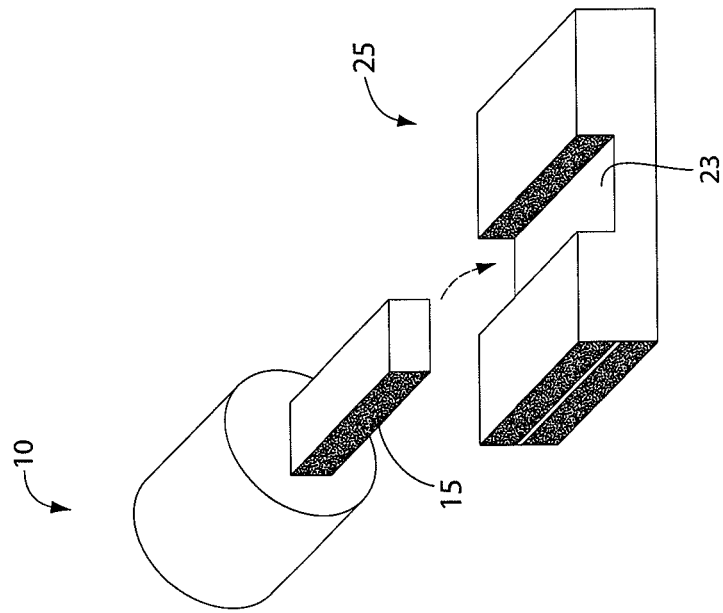
FIG. 23 is a perspective view of a lower end of the vessel of FIG. 22.
Figure 22:
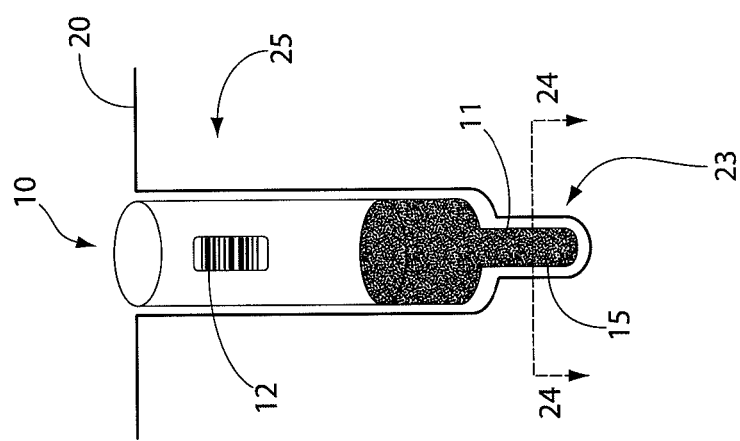
FIG. 22 is a side view of a vessel having an upper and a lower portion in a holder in accordance with yet another aspect of the invention.
Figure 24:
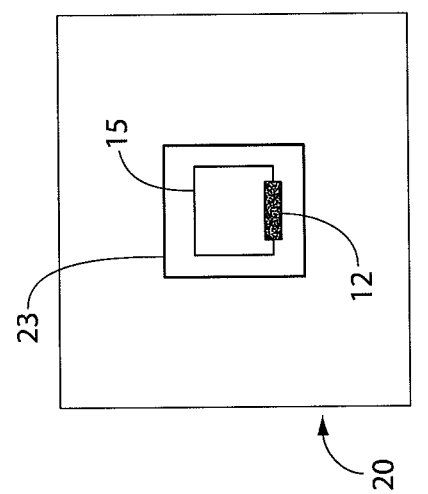
FIG. 24 is a section view of the lower end of the vessel of FIG. 22 in the holder.

Although the embodiments above show the positioning feature 15 located at or near a top of the vessel 10, the positioning feature 15 may include elements that are arranged in other ways. For example, the positioning element 15 may be located at or near a bottom of the vessel 10 and engage with a corresponding orientation feature 23 of the holder 20. For example, FIGS. 22-24 show a positioning feature 15 that has a generally rectangular box shape that depends from a bottom of the vessel 10. The holder 20 in this embodiment may have an orientation feature 23 that includes a rectangular hole near a bottom of an opening in the holder 20 that receives the vessel 10. The shapes of the positioning feature 15 and the orientation feature 23 may be arranged so that the vessel 10 will only be fully received by the holder when the positioning feature 15 is aligned with the orientation feature 23 so that the positioning feature 15 may extend into the orientation feature 23. In this embodiment, the rectangular cross-sectional shape of the positioning feature 15 may permit the positioning feature 15 to be received by the orientation feature 23 in any one of four different rotational positions (0 degrees, 90 degrees, 180 degrees, and 270 degrees rotation about the vessel's longitudinal axis, i.e., four alignment orientations), but other shapes for the positioning feature 15 may allow for full reception in the orientation feature 23 for only three different positions (e.g., for a triangular shape, i.e., three alignment orientations), only two different positions (e.g., for an elongated rectangular shape, i.e., two alignment orientations), or only one position (e.g., for an irregular shape). If the vessel 10 may be positioned in multiple different ways with respect to a holder 20, the reader 30 and/or the identification feature 12 may be arranged so that the identification feature 12 is read regardless of the final position of the vessel 10. For example, one or more readers 30 may be present for the identification region 12 of the vessel 10 to be read. Alternatively, in some embodiments, a reader 30 may move its position, allowing for an identification region 12 to be read at more than one alignment orientation.

Figure 25:
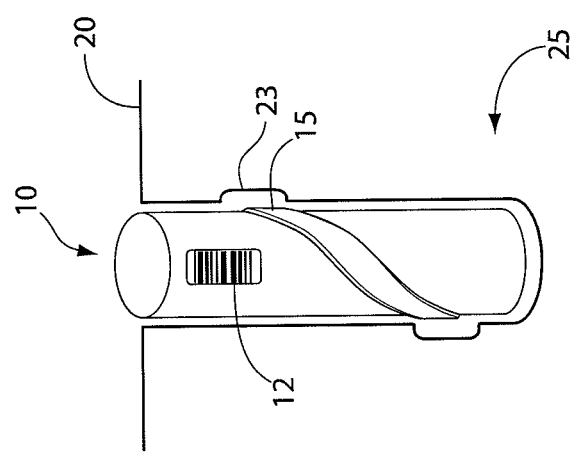
FIG. 25 is a side view of an embodiment of a vessel having a spiral portion in a holder in accordance with aspects of the invention.

In another illustrative embodiment, the vessel and/or the holder may include a positioning feature or orientation feature having a spiral type configuration. For example and as depicted in FIG. 25, the vessel 10 may include a positioning feature 15 that includes a spiral portion or thread and the holder 20 may include an orientation feature 23 that includes a spiral groove that receives the spiral positioning feature 15. As will be understood, when the vessel 10 is placed in the holder 20, the positioning feature 15 may engage with the orientation feature 23 so that as the vessel 10 drops, the vessel 10 also rotates about its longitudinal axis. When the vessel is located at a bottom of the opening of the holder 20, the identification feature 12 on the vessel 10 may be positioned for reading by the reader 30. Alternately, the identification feature 12 may be read by the reader 30 as the vessel is dropping and rotating into the holder 20. This type of configuration may help reduce or eliminate any requirement that the identification feature 12 be fixed on the vessel 10 in a particular way relative to the positioning feature 15. Of course, the positioning feature 15 and/or the orientation feature 23 may have other arrangements, such as having more threads incorporated into the positioning feature 15, the pitch of the thread may be adjusted, and so on. In some embodiments, friction between the vessel and the holder 20 may be minimized, for example, through added lubrication or application of an appropriate coating to either of or both surfaces. Such friction minimization allows for the vessel to more easily be placed into an alignment orientation for the identification region to be reliably read. In some embodiments, a vessel having a spiral portion is dropped into a holder and automatically settles into an alignment orientation such that the identification region may be read.

The positioning feature and/or the orientation feature may have various physical structure or arrangements including, but not limited to: a magnet or magnetizable material (e.g., so that the positioning and orientation features may be attracted/repelled so as to place the vessel in an alignment orientation), a gear form (e.g., so that the positioning and orientation features engage gear teeth to orient the vessel), projecting and/or recessed parts (such as the tab extensions and groove arrangements described above), corresponding shaped components that fit in a lock and key type arrangement (such as the D-shaped rim and opening in FIGS. 4-11), a detent arrangement (e.g., where the orientation feature includes a spring-loaded ball that engages with a positioning feature that includes a hemispherical or other suitably shaped groove in the vessel), a cam and cam follower arrangement (such as the orientation features and positioning features of FIGS. 12-21 where the orientation feature includes the cam in the form of a slanted portion and the positioning feature includes a cam follower in the form of a tab-like extension), a linkage (e.g., where the orientation feature includes a one or more bar linkage arrangement that serves to move or otherwise orient the vessel when contacted by the vessel's positioning element), and so on.

Having described several aspects of this invention, it should be appreciated that various alterations, modifications and improvements will occur to those of skill in the art. Such alterations, modifications and improvements are intended to be part of this disclosure and are intended to be within the spirit and scope of the invention. Thus, the description and drawings herein are intended to be illustrative, not limiting.

The phraseology and terminology used herein is for the purpose of description and should not be regarded as limiting. The use of "including," "comprising," "having," "containing," "involving," and/or variations thereof herein, is meant to encompass the items listed thereafter and equivalents thereof as well as additional items.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A system for handling and analyzing samples, the system comprising:
    a vessel for holding at least one biological sample, the vessel including an identification region for providing information related to the at least one sample, and the vessel having a positioning feature for placing the vessel in an alignment orientation;
    a holder for receiving the vessel, the holder including an orientation feature that complements the positioning feature of the vessel such that, with the vessel received in the holder, physical contact between the positioning feature and the orientation feature causes the vessel to move downward and rotate towards the alignment orientation relative to the holder such that a point fixed on the vessel moves around a longitudinal axis of the vessel; and
    a reader for reading the identification region of the vessel and storing the information related to the at least one sample when the vessel is moved to the alignment orientation,
    wherein:
    the orientation feature includes a cam and the positioning feature includes a cam follower; and
    the alignment orientation places the vessel in a position such that the identification region can be read by the reader.

2. The system of claim 1, wherein the vessel is rotatable about 360 degrees while the vessel is received by the holder.

3. The system of claim 2, further comprising a manipulator for rotating the vessel while the vessel is received by the holder.

4. The system of claim 1, wherein the positioning feature of the vessel comprises an extension that extends radially from the vessel.

5. The system of claim 1, wherein the positioning feature and the orientation feature includes complementary shaped elements that interact in a lock and key arrangement.

6. The system of claim 1, wherein the identification region comprises a bar code that represents an alphanumeric string.

7. The system of claim 1, wherein the orientation feature of the holder includes a stop feature for interacting with the positioning feature of the vessel and placing the vessel in the alignment orientation.

8. The system of claim 1, further comprising a vessel manipulator for physically manipulating the vessel and placing the vessel in the holder.

9. A method for handling and analyzing samples, the method comprising:
    providing a vessel for holding at least one sample, the vessel having an identification region for providing biological information related to the at least one sample, and a positioning feature for placing the vessel in an alignment orientation;
    placing the vessel in a holder having an orientation feature;
    causing the positioning feature and the orientation feature to interact such that, with the vessel received in the holder, physical contact between the positioning feature and the orientation feature causes the vessel to move downward and rotate towards the alignment orientation relative to the holder such that a point fixed on the vessel moves around a longitudinal axis of the vessel;
    reading the identification region of the vessel when the vessel is moved to the alignment orientation; and
    storing information related to the at least one sample, wherein:
    the orientation feature includes a cam and the positioning feature includes a cam follower; and
    the alignment orientation places the vessel in a position such that the identification region can be read by the reader 10. The method of claim 9, wherein causing the positioning feature and orientation feature to interact comprises rotating the vessel with a manipulator while the vessel is in the holder.

11. The method of claim 9, wherein the positioning feature comprises a rim with a flat, and the orientation feature includes an opening with a flat portion that complements the flat of the positioning feature.

12. A system for handling and analyzing samples, the system comprising:
    a vessel for holding at least one sample, the vessel having an identification region for providing biological information related to the at least one sample, and a positioning feature for placing the vessel in an alignment orientation, means for placing the vessel in a holder having an orientation feature;

means for causing the positioning feature and the orientation feature to interact such that, with the vessel received in the holder, physical contact between the positioning feature and the orientation feature causes the vessel to move downward and rotate towards the alignment orientation relative to the holder such that a point fixed on the vessel moves around a longitudinal axis of the vessel;

means for reading the identification region of the vessel when the vessel is moved to the alignment orientation; and means for storing information related to the at least one sample, wherein:

the orientation feature includes a cam and the positioning feature includes a cam follower; and the alignment orientation places the vessel in a position such that the identification region can be read by the reader.

13. The system of claim 1, wherein the orientation feature includes a slanted portion.

14. The system of claim 1, wherein the positioning feature includes an extension.

15. The system of claim 1, wherein the positioning feature includes a spiral portion and the orientation feature includes a spiral groove that receives the spiral portion of the positioning feature.

\* \* \* \* \*